US00PP08515P

United States Patent [19]

Saville

[11] Patent Number: Plant 8,515

[45] Date of Patent: Dec. 28, 1993

[54] MINIATURE ROSE PLANT NAMED SAVAFISH

[75] Inventor: F. Harmon Saville, Rowley, Mass.

[73] Assignee: Nor'East Miniature Roses, Inc., Rowley, Mass.

[21] Appl. No.: 940,507

[22] Filed: Sep. 4, 1992

[51] Int. Cl.[5] ..... A01H 5/00
[52] U.S. Cl. ..... Plt./10.1
[58] Field of Search ..... Plt. 10.1, 10, 9

[56] References Cited

U.S. PATENT DOCUMENTS

P.P. 6,456 12/1988 Bennett ..... Plt. 10
P.P. 7,188 3/1990 Bennett et al. ..... Plt. 10.1

*Primary Examiner*—Howard J. Locker
*Assistant Examiner*—Erich Veitenheimer
*Attorney, Agent, or Firm*—Christie, Parker & Hale

[57] ABSTRACT

A new miniature rose with bright orange red flowers.

1 Drawing Sheet

SUMMARY OF THE INVENTION

The present invention relates to a new and distinct variety of rose plant of the miniature rose class, which was created by me by crossing as seed parent the variety known as 'Fairlane' and as pollen parent the variety known as 'Zorina'. The varietal denomination of this new rose is 'Savafish'.

Among the novel characteristics possessed by this new variety which distinguishes it from its parent and all other varieties of which I am aware is its unusual bright orange red flowers of attractive form.

Asexual reproduction by propagation of cuttings of the new variety as performed in Essex County, Mass. shows that the foregoing and other distinguishing characteristics come true to form and are established and transmitted through succeeding propagations.

BRIEF DESCRIPTION OF ILLUSTRATION

The accompanying illustration shows typical specimens of the flowers of the new variety in different stages of development depicted in color as nearly true as it is reasonably possible to make the same in a color illustration of this character.

DETAILED DESCRIPTION OF THE NEW VARIETY

The following is a detailed description of my new variety, with color terminology in accordance with The Royal Horticultural Society Colour Chart (R.H.S.C.C.). The terminology used in color description herein refers to plate numbers in the aforementioned color chart.

Parentage:
*Seed parent.*—'Fairlane'.
*Pollen parent.*—'Zorina'.
Class: Miniature.

The following observations are made of specimens grown outdoor in Essex County, Mass., during the month of July; however, it is recognized that dimensions vary depending on time of the year, climate, amount of sun (light) preceding bloom, temperature and cultivation practices.

Flower

Blooming habit: Recurrent.

A. Bud:
(1) *Size.*—Small, about ⅝-inch by ½-inch wide, when sepals first divide.
(2) *Form.*—Ovoid.
(3) *Color.*—As sepals divide, bud color is near 34A.
(4) *Sepals.*—Slightly foliated, slightly longer than bud.
(5) *Peduncle.*—Length — about 1⅛ inches. Aspect — straight. Strength — erect. Color — near 144B.

B. Bloom:
(1) *Size.*—Average size when fully open — about 1⅛ inches to 1½ inches wide by ⅝-inch wide.
(2) *Borne.*—Singly and several together in sprays; blooms are mostly borne singly, however there are some sprays of 3 to 5 blooms; in first bloom in spring after coming out of dormancy there are occasional sprays of as many as 10 to 20 blooms.
(3) *Form.*—Flat, reflexing outward, outer petals quill to points, inner petals with pronounced apices.
(4) *Petalage.*—Number of petals under normal conditions — about 25 to 32.
(5) *Color.*—After sepals divide and petals begin to unfurl, petal color tends to near 33A, with coloration where petals bunch appearing somewhat darker, near 34A. Color at point of petal attachment is near 12A. General tonality from a distance is bright orange. Color lightens somewhat as flowers age, becoming near 33C to 33D.

C. Petals:
(1) *Texture.*—Average.
(2) *Appearance.*—Inside velvety and outside satiny.
(3) *Form.*—Fan shaped.
(4) *Arrangement.*—Imbricated.
(5) *Petaloids in center.*—Medium.
(6) *Persistence.*—Drop off cleanly.
(7) *Fragrance.*—Slight.
(8) *Lasting quality.*—Long lasting on plant.

Reproductive Organs

A. Arrangement of stamens, filaments and anthers: Regularly arranged around styles.
*Color.*—Near 20A.

B. Pollen:
*Color.*—Near 24C.
C. Styles: Uneven length, thin.
D. Stigmas:
*Color.*—Near 145C.
E. Hips: None observed.

Plant

A. Form: Compact.
B. Growth: Very vigorous, uniform branching.
*Height attained.*—About 14 to 18 inches; plant width attained in Rowley, Mass. is about 15 to 16 inches.
C. Foliage: Compound 5 to 7 leaflets.
(1) *Size.*—Medium.
(2) *Quantity.*—Abundant.
(3) *Color.*—New foliage: Upper side — near 143A. Underside — near 146C. Old foliage: Upper side — near 137A. Underside — near 138B.
(4) *Shape.*—Oval, pointed.
(5) *Texture.*—Upper side is glossy; underside is matte.
(6) *Edge.*—Serrated.
(7) *Serration.*—Quite even, shallow.

(8) *Leaf stem.*—Color — near 143A. Under side — 144A.
(9) *Stipules: Medium length, slightly bearded.*
(10) *Resistance to disease: Blackspot — Very good. Mildew — Very good. Rust — Very good.*
D. Wood:
(1) *New wood.*—Color — near 143B. Bark — smooth.
(2) *Old wood.*—Color — near 144A. Bark — smooth.
E. Thorns:
(1) *Thorns.*—Quantity (main stalk) — ordinary. On laterals from stalk — ordinary. Form — long, thin, straight point. Length — medium. Color — near 145C. Position — irregular.
(2) *Prickles.*—none.
F. Winter hardiness: Needs protection in severe climates.

I claim:

1. A new and distinct variety of rose plant of the miniature rose class, substantially as shown and described.

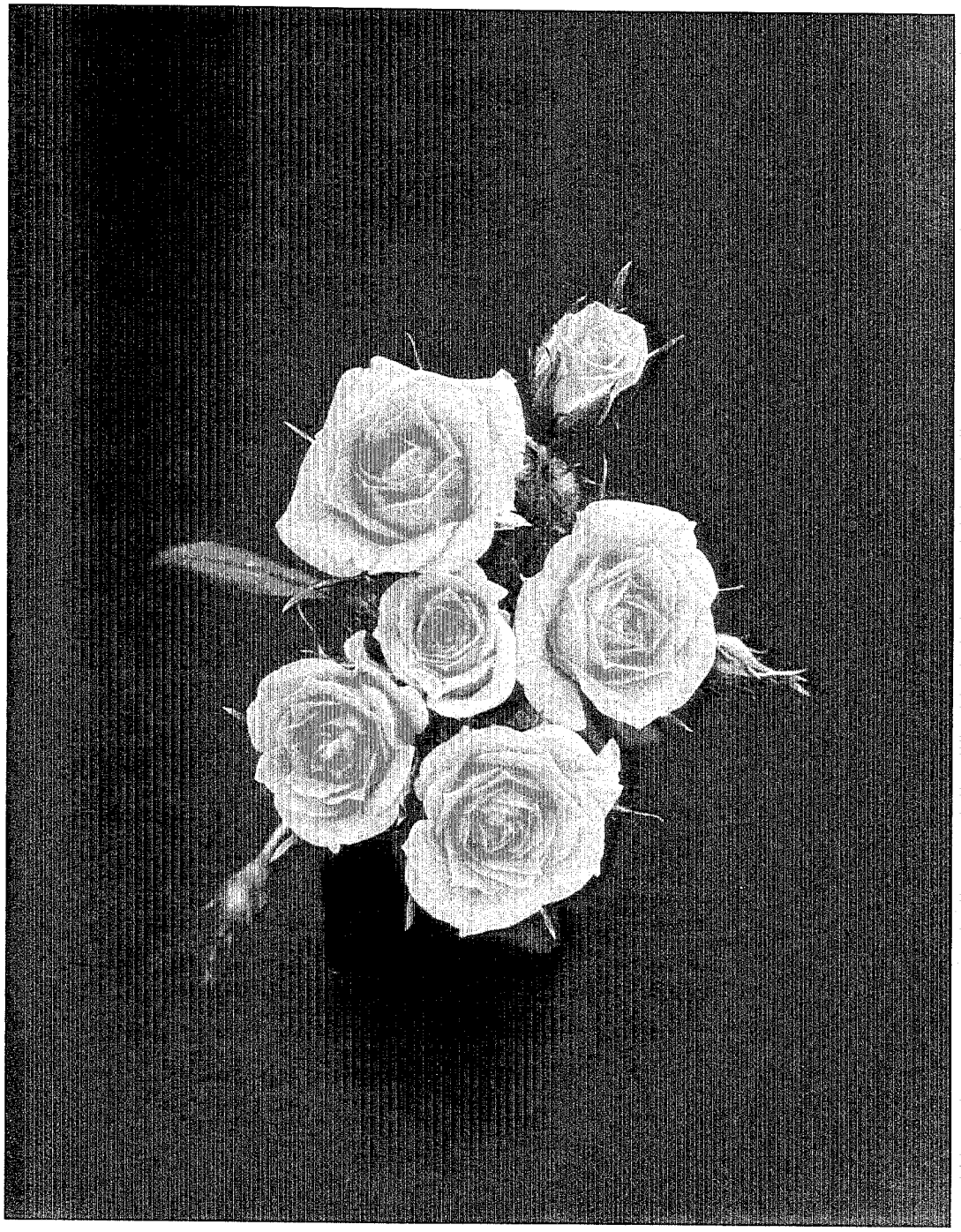

* * * * *